United States Patent

Gross et al.

[11] Patent Number: 5,962,047
[45] Date of Patent: *Oct. 5, 1999

[54] MICROCRYSTALLINE STARCH-BASED PRODUCT AND USE IN FOODS

[75] Inventors: Akiva Gross, Newton; Stephen G. Haralampu, Plymouth, both of Mass.

[73] Assignee: Opta Food Ingredients, Inc., Bedford, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/665,082

[22] Filed: Jun. 14, 1996

[51] Int. Cl.$^6$ .................................... A23L 1/076
[52] U.S. Cl. ........................ 426/48; 426/549; 426/658; 426/661
[58] Field of Search ................... 426/48, 49, 52

[56] References Cited

U.S. PATENT DOCUMENTS

| | | | |
|---|---|---|---|
| 3,023,104 | 2/1962 | Battista | 99/1 |
| 3,666,557 | 5/1972 | Jensen et al. | 127/32 |
| 3,730,840 | 5/1973 | Sugimoto et al. | 195/31 |
| 3,766,011 | 10/1973 | Kurimoto et al. | 195/31 |
| 4,308,294 | 12/1981 | Rispoli et al. | 426/564 |
| 4,510,166 | 4/1985 | Lenchin et al. | 426/565 |
| 4,726,957 | 2/1988 | Lacourse et al. | 426/578 |
| 4,956,193 | 9/1990 | Cain et al. | 426/573 |
| 5,051,271 | 9/1991 | Iyengar et al. | 426/658 |
| 5,281,276 | 1/1994 | Chiu et al. | 127/65 |
| 5,409,542 | 4/1995 | Henley et al. | 127/65 |

FOREIGN PATENT DOCUMENTS

| | | |
|---|---|---|
| 480 433 | 4/1992 | European Pat. Off. . |
| 564893A1 | 10/1993 | European Pat. Off. . |
| 616779A1 | 9/1994 | European Pat. Off. . |
| 0688872A1 | 12/1995 | European Pat. Off. . |
| 688872A1 | 12/1995 | European Pat. Off. . |
| 89/09793 | 10/1989 | WIPO . |
| 90/15147 | 12/1990 | WIPO . |
| 91/07106 | 5/1991 | WIPO . |
| 92/21703 | 12/1992 | WIPO . |
| 94/09645 | 5/1994 | WIPO . |
| 94/14342 | 7/1994 | WIPO . |
| 95/04082 | 2/1995 | WIPO . |

OTHER PUBLICATIONS

Jane and Robyt, "Structure Studies of Amylose–V Complexes and Retrograded Amylose by Action of Alpha Amylases, and a New Method for Preparing Amylodextrins", *Carbohydrate Research* 132:105–118 (1984).

Englyst and Cummings, "Digestion of the Polysaccharides of Some Cereal Foods in the Human Small Intestine", *Am. J. Clin. Nutr.* 42:778–787 (1985).

Annison and Topping "Nutritional Role of Resistant Starch: Chemical Structure vs Physiological Function", *Annu. Rev. Nutr.* 14:297–320 (1994).

D. Sievert and Y. Pomeranz, "Enzyme–Resistant Starch.I. Characterization and Evaluation by Enzymatic, Thermoanalytical, and Microscopic Methods", *Cereal Chem.* 66(4):342–347 (1989).

H.N. Englyst et al., "Dietary Fiber and Resistant Starch", *Am. J. Clin. Nutr.* 46:873–874 (1987).

J.H. Cummings et al., "Digestion and physiological properties of resistant starch in the human large bowel", *Br. J. Nutr.* 75:733–747 (1996).

*Primary Examiner*—Donna C. Wortman
*Assistant Examiner*—Brenda G. Brumback
*Attorney, Agent, or Firm*—Hamilton, Brook, Smith & Reynolds, P.C.

[57] ABSTRACT

A microcrystalline starch-based product comprising microcrystalline starch, glucose and short chain glucooligosaccharides and having an average particle size of less than about 10 $\mu$, and a process for making the microcrystalline starch-based product consisting of optionally debranching, retrograding and hydrolyzing a starch are disclosed. Also disclosed are food formulations comprising the microcrystalline resistant starch-based product.

17 Claims, No Drawings

MICROCRYSTALLINE STARCH-BASED PRODUCT AND USE IN FOODS

BACKGROUND OF THE INVENTION

Microcrystalline cellulose has been used in the food industry as a popular component in stabilizer systems for ice cream and other frozen food products. U.S. Pat. No. 3,023,104 (Battista) teaches the use of microcrystalline cellulose as a texturizing agent for an ice cream-like product. Although the product exhibits good functionality, microcrystalline cellulose suffers from some negative consumer impressions linked to the use of processed cellulose, especially from wood pulp, as a food ingredient.

It would therefore be advantageous to produce a microcrystalline starch product, which behaves functionally like its cellulose counterpart, but possesses the positive labeling attribute of being viewed as more a "natural" or "usual" food ingredient in the eyes of the consumer. Microcrystalline starch is based on resistant starch technology; for example, U.S. Pat. No. 5,051,271 (Iyengar et al.) teaches a starch-derived, food-grade, insoluble bulking agent which is produced by heating, optionally debranching and then hydrolyzing a polysaccharide and subsequently washing the product to remove enzymes or acids, water-soluble sugars and glucooligosaccharides. The particular processing steps ensure a small particle size, which is critical to the smooth texture of a product such as ice cream.

SUMMARY OF THE INVENTION

The present invention relates to a food-grade, microcrystalline resistant starch-based product comprising microcrystalline starch, glucose and short chain glucooligosaccharides and having a median particle size of less than about 10 $\mu$, and to a process for making the microcrystalline resistant starch-based product. The process involves retrogradation of a hydrated, optionally debranched starch, followed by enzymatic or chemical hydrolysis to reduce or remove the amorphous regions of the starch molecule. The resulting product contains retrograded starch microcrystals, glucose and short chain glucooligosaccharides; the product is typically dried to produce a powder.

The retrogradation step of the present process involves hydrating starch in an aqueous solution at elevated temperatures, followed by incubation, and optionally annealing, at lower temperatures thereby causing the formation of crystalline regions in the starch molecule. Optionally, prior to or during retrogradation, the starch may be debranched, preferably by enzymes, to enhance the retrogradation process. The retrograded starch produced is then hydrolyzed either by enzyme or acid to yield a mixture of water-insoluble microcrystalline starch, water-soluble glucose and short chain glucooligosaccharides.

The microcrystalline starch has a small particle size, typically less than 10 $\mu$ and preferably less than 6 $\mu$, and a smooth consistency. The resulting product may also be co-processed with hydrocolloids or other ingredients known in the art. The properties of the product can be changed by varying the type of starch used, and the extent of retrogradation and/or hydrolysis of the amorphous regions.

The microcrystalline starch-based product of the present invention can be used in a variety of food products and beverages. The product can act as a sweetening agent for food and beverage products in which it is incorporated as a result of the glucose and glucooligosaccharides. Foods and beverages which can be formulated with the microcrystalline starch-based product of the present invention include cookies, breads, cakes, pies, noodles, fudge, brownies, low-fat margarine, snack dips, sour cream, mayonnaise, cream cheese and other spreads, yogurt, milkshakes, ice cream and frozen desserts. The microcrystalline starch-based product can also be included in snack item formulations such as crackers, graham crackers, pretzels and similar products, as well as extruded foods such as extruded cereals and snacks. The microcrystalline starch-based product of the present invention is also suitable for inclusion in nutritional and dietary drinks, as well as in foods which are useful for the slow release of glucose, such as for diabetics. The microcrystalline starch-based product is also useful as a component of a stabilizer complex in frozen foods to control ice crystal formation. The product of the present invention can be used in sugar-free foods as well; the amount of sugar, flour or fat in a given formulation which can be replaced with the microcrystalline starch-based product will depend in part on the formulation, the desired properties of the food and the amount of calorie and/or fat reduction or fiber content desired. The product of the present invention can also be added as an extender to a formulation without reducing any of the other ingredients. The extended product has a lower calorie or fat content per volume compared with the unextended product.

DETAILED DESCRIPTION OF THE INVENTION

The present invention relates to a microcrystalline resistant starch-based product and to a process for making the microcrystalline starch-based product. The product of this invention has a small particle size (typically less than 10 $\mu$ and preferably less than about 6 $\mu$) and a smooth consistency. The microcrystalline starch-based product can be incorporated into many foods and beverages as a bulking agent to add bulk to the product without adding significant fat or calories, as a fat, sugar and/or flour replacer or as a component in a stabilizer complex in frozen foods, particularly to prevent the formation of ice crystals.

As used herein, the terms "non-fat" and "fat-free" are intended to mean a product that contains less than 0.5 gram total fat per 30 gram serving. The term "reduced fat" is intended to mean herein a product having greater than or equal to a 25% reduction in fat compared to the full fat equivalent. The term "low fat" is intended to mean herein a product that contains 3 grams of total fat per 50 gram serving. These definitions are consistent with the definitions of "fat free", "reduced fat" and "low fat" as set forth by the Nutrition Labeling and Education Act (NLEA), Federal Register, Jan. 6, 1993.

In the first step of the process, starch is hydrated to allow for sufficient molecular mobility for retrogradation to occur. The hydration step may only swell the native starch granules, or may fully rupture the granules and solubilize the starch, depending upon the time and temperature conditions used. Thereafter, the starch is subjected to retrogradation, during which it undergoes a physical transition that results in a new structure in which microcrystalline, double-helical regions (retrograded regions) are interspersed with amorphous regions. Optionally, prior to or during retrogradation, the starch may be debranched, preferably by enzymes, to enhance the retrogradation process. The retrograded starch is further modified by hydrolysis of the amorphous, non-crystalline regions. In the hydrolysis step, the product is treated with an appropriate catalyst (e.g., a glucosidase, such as glucoamylase or $\alpha$-amylase, or mixture thereof, or an acid) to hydrolyze the amorphous regions to glucose and short chain glucooligosaccharides, while leaving the resistant microcrystalline regions intact.

The resulting product is a microcrystalline starch-based product which has a low degree of amorphous starch regions. That is, the material is comprised mostly of retrograded microcrystalline starch, glucose and short chain glucooligosaccharides. Preferably, less than about 10% by weight of the product will be amorphous starch regions. The structure of the final material, and/or its functional properties depend in part on the specificity of the enzyme used and the degree of hydrolysis. Thus the amount of amorphous material which remains attached to the microcrystalline regions can be controlled by the choice of glycosidase enzyme, and by controlling the conditions of the enzyme-mediated or acid-mediated hydrolysis step.

Any native or pregelatinized starch can be used as the starting material of the present invention. Particularly preferred starches are high amylose starches, most preferably starches containing at least 30% amylose, when measured by iodine binding (Schoch, T. J., *Methods in Carbohydrate Chemistry* 4:157–160 (1964)). Suitable starches include corn, potato, wheat, rice, barley, tapioca, cassava, arrowroot, sago and oat starches. For example, a hybrid of corn starch, such as starch from the ae7 hybrid of corn, available under the trade names AMYLOMAIZE VII® (Cerestar USA, Inc., Hammond, Ind.) and HYLON VII® (National Starch and Chemical Company, Bridgewater, N.J.), is a particularly suitable starch. This starch will assay to less than about 20% TDF (total dietary fiber) and when analyzed by differential scanning calorimetry (DSC) exhibits thermal activity peak (gelatinization) from about 55° C. to 130° C. with a peak at about 95° C. and total peak enthalpy of about 24 J/g. Typically the starch will have an amylose content of from about 65% to about 75%.

The first step of the process is performed by dispersing an appropriate starch in an aqueous medium, such as water or a buffer, or a mixture of water and an organic solvent (e.g., alcohol or DMSO) containing at least about 80% by volume of water. The suspension generally contains up to about 40% (w/v) starch. The dispersion is then heated, preferably to a temperature in the range of from about 50° C. to about 130° C., for a time sufficient to hydrate the starch by methods known in the art, such as batch heating, jet cooking or continuous cooking. The extent of hydration may range from a partial swelling of the starch granule to complete disruption and solubilization of the starch, depending upon the time and temperature conditions used. If the hydration is carried out at the low end of the temperature range, the cooked product will remain fairly opaque, and the achievable level of resistant starch may be somewhat reduced.

The dispersion of hydrated starch is then incubated at an elevated temperature, preferably from about 50° C. to about 120° C. for a period of time sufficient to cause retrogradation to occur (e.g., from about 4 to 100 hours). The incubation may be isothermal, or may cycle between high and low temperature limits to promote rapid and complete formation of microcrystals.

Since the formation of stable starch microcrystals is believed to involve only straight chain amylose molecules, it is useful, though not essential, to debranch the amylopectin fraction of the native starch, thereby enhancing the retrogradation process. Debranching may occur prior to or concurrent with the retrogradation step. The conversion can be accomplished by the use of debranching enzymes such as α-1,6 specific glucosidases (e.g., pullulanase or isoamylase or mixtures thereof). PROMOZYME® 200 (Novo Nordisk Biochem North America, Inc. Franklinton, N.C.) is a commercial enzyme preparation particularly useful for the present process. Partial hydrolysis of the polysaccharide chain, i.e., partial hydrolysis of the α-1,4 linkages such as by an α-amylase, may also be useful in the process to create a specific molecular weight distribution which maximizes the yield of microcrystalline product.

The retrograded starch is then hydrolyzed to reduce or eliminate the amorphous starch regions, leaving the water-insoluble, resistant microcrystalline starch regions along with water-soluble glucose and short chain glucooligosaccharides with a degree of polymerization (DP) of less than 20. Hydrolysis can be accomplished enzymatically (e.g., using a glycosidase) or chemically (e.g., using an acid). A glycosidase enzyme, a mixture thereof, or an acid is added to a suspension of the retrograded starch in an aqueous medium, e.g., water or a buffer, and the reaction mixture is incubated with stirring until the desired degree of hydrolysis is achieved, generally from about 1 to about 30 hours.

The amount of enzyme added will vary, depending upon the identity and activity of the enzyme or enzyme mixture used and the process conditions (e.g., time, temperature, pH). The amount will generally be sufficient to complete hydrolysis of the amorphous, non-microcrystalline starch regions in less than about 30 hours. Acids which can be used in the hydrolysis step are those generally used to hydrolyze carbohydrates, which include mineral acids such as HCl and $H_2SO_4$, and organic acids such as acetic acid or trifluoracetic acid. Acid concentrations appropriate in this step of the process are generally about 0.2 N. Higher concentrations can be used but generally do not result in faster hydrolysis, and may produce undesirable side reactions.

The reaction temperature during the hydrolysis step will generally be from about 10° C. to about 100° C. Since the enzyme will remain in the product, it is advisable to inactive the enzyme by acid or heat or a combination of both, so that residual activity does not limit the use of the microcrystalline starch-based product in food applications. Enzyme inactivation protocols are known to those skilled in the art, or may be obtained from commercial enzyme suppliers.

The microcrystalline starch-based product, comprising microcrystalline starch, glucose and short chain glucooligosaccharides, can optionally be dried to a powdered form. Suitable methods in the art include, but are not limited to, spray drying, drum drying, or flash drying. The dried microcrystalline starch-based product can be rehydrated in an aqueous medium with medium shear to produce a dispersion with a smooth consistency.

Adjuncts may be added to the microcrystalline starch-based product prior to drying or can be dry blended with the final product. For example, hydrocolloids, gums, polymers, modified starches and combinations thereof can be added to the product to change the rheology or increase the water binding capacity of the product. The adjuncts can also be added to enhance functional properties for a fully functional stabilizer system, e.g., to build viscosity or for emulsification. Adjunct ingredients suitable for use in the invention include xanthan, alginate, carrageenan, carboxymethyl cellulose, methyl cellulose, guar gum, gum arabic, locust bean gum and combinations thereof.

The microcrystalline starch-based product of the present invention is comprised of greater than about 20%, and preferably greater than about 30%, microcrystalline starch, along with glucose and short chain glucooligosaccharides. The product may also have a small amount, e.g., less than about 10 percent, of amorphous starch, depending upon the extent of hydrolysis. The microcrystalline starch-based product meets the requirements for the category of dietary fiber and is perceived by consumers as a natural product, since no chemical alteration other than hydrolysis of the starch starting material occurs. The product has a particle size of less than about 10 $\mu$, and preferably less than about 6 $\mu$. The non-dried or rehydrated microcrystalline starch-based product has a smooth consistency and wide ranging water-holding capacity and digestibility.

The microcrystalline starch-based product can be incorporated into food and beverage formulations in either the aqueous or dried form, depending upon the food formulation. The microcrystalline starch-based product can be used as a dietary fiber supplement, as a replacement or substitute for sugar and/or flour, as a fat extender in low-fat or fat-free food formulations, as a tabletting aid, and as a component of a stabilizer complex in frozen foods to control ice crystal formation.

The microcrystalline starch-based product of the present invention can be used in a variety of food products and beverages. The product can act as a sweetening agent for food and beverage products in which it is incorporated as a result of the glucose and glucooligosaccharides. Foods and beverages which can be formulated with the microcrystalline starch-based product of the present invention include cookies, breads, cakes, pies, noodles, fudge, brownies, low-fat margarine, snack dips, sour cream, mayonnaise, cream cheese and other spreads, yogurt, milkshakes, ice cream and frozen desserts such as ice cream, sherbet, ice milk, frozen yogurt and POPSICLE™S. The microcrystalline starch-based product can also be included in snack item formulations such as crackers, graham crackers, pretzels and similar products, as well as extruded foods such as extruded cereals and snacks. The microcrystalline starch-based product of the present invention is also suitable for inclusion in nutritional and dietary drinks, as well as in foods which are useful for the slow release of glucose. The product of the present invention can be used in sugar-free foods as well; the amount of sugar, flour or fat in a given formulation which can be replaced with the microcrystalline starch-based product will depend in part on the formulation, the desired properties of the food and the amount of calorie and/or fat reduction or fiber content desired. The product of the present invention can also be added as an extender to a formulation without reducing any of the other ingredients. The extended product has a lower calorie or fat content per volume compared with the unextended product.

The following Examples are offered for the purpose of illustrating the present invention and are not to be construed to limit the scope of this invention. The teachings of all references cited herein are hereby incorporated herein by reference.

EXAMPLES

Production of Microcrystalline Starch-Based Product With Annealing

A slurry of 15.2 kg HYLON® VII (National Starch and Chemical Company, Bridgewater, N.J.) high amylose corn starch in 75.8 kg water was prepared in a jacketed, Breddo LIKWIFIER® (American Ingredients Company, Kansas City, Kans.) and measured to have a pH of 5.2. The slurry was heated with hot water in the kettle jacket to 90° C. under agitation. The slurry was then cooked by continuous steam injections in a Hydroheater (Hydro-Thermal Corporation, Waukesha, Wis.) equipped with a holding tube of about 1 minute residence. The slurry was cooked at 160° C. into a hemispherical bottom, jacketed, scraped-surface vessel. After cooking the starch mixture was cooled to 60° C. The pH was measured to be 5.3 and was adjusted to 5.1 with dilute phosphoric acid.

The starch was debranched with pullulanase (258 ml PROMOZYME® 200L; Novo Nordisk Biochem North America, Inc., Franklinton, N.C.). The reaction proceeded for 4 hours at 60° C. The enzyme was inactivated after 4 hours by heating the mixture to 90° C. for 30 minutes.

The debranched starch was retrograded and annealed by rapid cooling to 60° C., following by heating to 90° C. and holding for 30 minutes. This 60° C. to 90° C. cycle was repeated 3 times. On the third cycle, the mixture was held at 90° C. for about 2 hours and slowly cooled to 55° C. over a 4 hour period, and then held at 55° C. for about 9 hours.

A portion of the mixture containing 10.9 kg starch was diluted from 17% to 14% solids. The pH was adjusted to 4.8 with dilute phosphoric acid and the amylase mixture was added. The mixture contained 109 ml each of CLARASE® L-40,000 ($\alpha$-amylase) and DIAZYME® L-200 (glucoamylase, both enzymes supplied by Solvay Enzyme Products, Inc., Elkhart, Ind.). The hydrolysis reaction proceeded for 4 hours at 55° C. The enzymes were inactivated by heating the mixture to 90° C.

The microcrystalline starch mixture was spray dried to a powder, which assayed as 38% total dietary fiber (TDF) by the Prosky Method (AACC Method 32-07) and was comprised of 9 $\mu$ retrograded starch microcrystals as measured on a Microtrac (Leeds and Northrup Instruments, North Wales, Pa.).

Production of Microcrystalline Starch-Based Product Without Anealing

A slurry of 11.4 kg HYLON® VII, high amylose corn starch in 56.8 kg water was prepared in a jacketed, Breddo LIKWIFIER®. Hot water in the kettle jacket heated the slurry to 90° C. under agitation. The slurry was then cooked by continuous steam injection in a Hydroheater equipped with a holding tube of about 1 minute residence. The slurry was cooked at 160° C. into a hemispherical bottom jacketed, scraped-surface vessel. A total of 9.2 kg starch (dry basis) was recovered from the jet-cooking operation. After cooking, the starch mixture was cooled to 58° C., and the pH was 5.3.

The starch was debranched with 183 ml pullulanase (PROMOZYME® 200L). The reaction proceeded for 4 hours at 58° C., after which the enzyme was inactivated by heating the mixture to 90° C. and holding for 1 hour.

The debranched starch was retrograded by slow cooling to 55° C. over a 17 hour period. The non-crystalline regions of the retrograded starch were digested with 92 ml CLARASE® L-40,000 at 55° C. for a period of about 24 hours. The enzymes were inactivated by heating the mixture to 90° C.

To enhance the stabilizer function for ice cream, 10% carboxymethyl cellulose (CMC) was added to the microcrystalline starch slurry. A CMC solution was made by dissolving 909 g AQUALON®, Type 7MF (Hercules Incorporated, Wilmington, Del.) in 45.5 kg water at 90° C. and mixing vigorously for 1 hour. The microcrystalline starch slurry was added to the CMC solution and agitated vigorously for an additional 30 minutes while the temperature was maintained at 90° C. The mixture was spray dried.

The powdered microcrystalline starch product assayed as 32% TDF by the Prosky Method and was comprised of 6 $\mu$ retrograded starch microcrystals as measured on a MICROTRAC®.

Production of Microcrystalline Starch-Based Product Without Annealing and With Less Extensive Hydrolysis of Amorphous Regions A slurry of 11.4 kg HYLON® VII, high amylose corn starch in 56.8 kg water was prepared in a jacketed, Breddo LIKWIFIER®. Hot water in the kettle jacket heated the slurry to 90° C. under agitation. The slurry had a pH of 5.3. The slurry was then cooked by continuous steam injection in a Hydroheater equipped with a holding tube providing about 1 minute residence. The slurry was cooked at 160° C. into a hemispherical bottom, jacketed, scraped-surface vessel. A total of 9.3 kg starch (dry basis) was recovered from the jet-cooking operation. After cooking the starch mixture was quickly cooled to 58° C., and the pH was measured at 5.1.

The starch was debranched with 186 ml pullulanase (PROMOZYME® 200L). The reaction proceeded for 4 hours at 58° C. After which, the enzyme was inactivated by heating the mixture to 90° C. and holding for 2 hours.

The debranched starch was retrograded by slow cooling to 55° C. over a 4 hour period, and held at 55° C. for an additional 10 hours. The non-crystalline regions of the retrograded starch were digested with 93 ml CLARASE® L-40,000 at 55° C. for a period of about 4 hours. The enzyme was inactivated by heating the mixture to 90° C.

The microcrystalline starch assayed as 33% TDF by the Prosky Method and was comprised of 7.6 $\mu$ retrograded starch microcrystals as measured on a MICROTRAC®.

To enhance the stabilizer function for ice cream, 10% carboxymethyl cellulose (CMC) was added to the microcrystalline starch slurry. A CMC solution was made by dissolving 466 g AQUALON®, Type 7MF in 18.2 kg water at 90° C. The microcrystalline starch slurry, representing 4.7 kg of the original starch solids in the process, was added to the CMC solution and agitated vigorously for 30 minutes while the temperature was maintained at 90° C. The mixture was spray dried.

Production of Microcrystalline Starch-Based Product Without Complete Disruption of Starch Granule A 25% starch slurry was prepared by blending 14.5 kg HYLON® VII and 39.3 kg water in a scraped-surface, hemispherical bottom, jacketed kettle at a pH of 5.2. The slurry was heated to 90–100° C. and held for 2 hours to swell the starch granules, after which the slurry was cooled to 57° C. The pH dropped to 4.9 during the cooking operation.

The starch was debranched with PROMOZYME® 200L at a level of 5% on a starch basis, or 727 ml. The mixture was held at 57° C. and agitated for 21 hours, during which time the starch retrograded. The PROMOZYME® 200L was inactivated by heating the mixture to 90° C. and holding for 2 hours. The mixture was then hydrolyzed to form the microcrystalline starch with a combination of 145 ml of CLARASE® L-40,000 ($\alpha$-amylase) and 145 ml DIAZYME® L-200 (glucoamylase, both enzymes supplied by Solvay Enzyme Products, Inc., Elkhart, Ind.) at 55° C. for 16 hours. These enzymes were inactivated by heating the mixture to 90° C. prior to spray drying.

The final product was analyzed to be 30.0% TDF, with a median particle size (weight basis) of 9.4 $\mu$.

Preparation of No-Fat Ice Cream

The microcrystalline starch-based product of Example 2 was used to make a no-fat ice cream product. The microcrystalline starch-based product was compared to AVICEL® (FMC Corporation, Philadelphia, Pa.) in the following formulations:

| Ingredient | 1 | 2 | 3 |
|---|---|---|---|
| Skim milk | 23.24 kg | 23.24 kg | 23.24 kg |
| Non-fat dry milk | 2.04 | 2.04 | 2.04 |
| Sugar | 3.86 | 3.86 | 3.86 |
| Maltodextrin (5 DE) | 1.45 | 1.45 | 1.45 |
| Corn syrup solids (36 DE) | 1.09 | 0.83 | 0.83 |

-continued

| Ingredient | 1 | 2 | 3 |
|---|---|---|---|
| Stabilizer | 0.08 | 0.08 | 0.08 |
| Mono- & diglycerides | 0.06 | 0.06 | 0.06 |
| AVICEL ® RC581 | 0.00 | 0.26 | 0.00 |
| Microcrystalline starch-based product | 0.00 | 0.00 | 0.26 |
| TOTAL | 31.56 kg | 31.82 kg | 31.82 kg |

The dry ingredients were dispersed in the liquid using an overhead stirrer for about 5 minutes. The mixture was then pasteurized in a regenerating plate heat exchanger (APV/Crepaco) in which the pre-mix was heated to 71° C. in the regeneration portion of the heat exchanger and homogenized through a 2-stage homogenizer (2000 psi first stage/500 psi second stage; APV/Gaulin, Wilmington, Mass.), followed by pasteurization at 85° C. for 25 seconds, before being cooled to 4° C. The pre-mixes were aged overnight at 4° C.

The ice cream pre-mixes were frozen in a continuous ice cream freezer (PMS, Philadelphia, Pa.) operating at –7° C., packed in 946 ml containers and hardened overnight at –40° C.

A trained sensory panel evaluated ice cream formulations 2 and 3 to be similar in quality, and ice cream formulation 1 to be colder and icier.

Preparation of Low Fat Ice Cream

The microcrystalline starch-based product of Example 3 were used to make a low-fat ice cream product. The microcrystalline starch-based product was compared to AVICEL® RC581 in formulations of the following compositions:

| Ingredient | 1 | 2 | 3 |
|---|---|---|---|
| Fat | 0.97 kg | 0.97 kg | 0.97 kg |
| Milk solids, non fat | 3.58 | 3.58 | 3.58 |
| Sugar | 4.38 | 4.38 | 4.38 |
| Corn syrup solids (36 DE) | 1.79 | 1.79 | 1.79 |
| Maltodextrin (5DE) | 0.26 | 0.0 | 0.0 |
| Guar gum | 0.05 | 0.05 | 0.05 |
| Carrageenan | 0.006 | 0.006 | 0.006 |
| Mono- & diglycerides | 0.065 | 0.065 | 0.065 |
| AVICEL ® RC581 | 0.0 | 0.26 | 0.0 |
| Microcrystalline starch-based product | 0.0 | 0.0 | 0.26 |
| TOTAL (kg) | 11.101 | 11.101 | 11.101 |

The dry ingredients were dispersed in the liquid using an overhead stirrer for about 5 minutes. The mixture was then pasteurized in a regenerative plate heat exchanger (APV/Crepaco) in which the pre-mix was heated to 71° C. in the regeneration portion of the heat exchanger and homogenized through a 2-stage homogenizer (2000 psi first stage/500 psi second stage; APV/Gaulin, Wilmington, Mass.), followed by pasteurization at 85° C. for 25 seconds, before being cooled to 4° C. The pre-mixes were aged overnight at 4° C.

The ice cream pre-mixes were frozen in a continuous ice cream freezer (PMS, Philadelphia, Pa.) operating at –7° C., packed in 946 ml containers and hardened overnight at –40° C.

A trained sensory panel evaluated the ice cream samples initially (time zero) and after 6 weeks of accelerated storage. There were no significant differences between the ice creams at time zero. After 6 weeks of accelerated storage (accelerated by fluctuating the temperature in a 3 hour cycle between –23° C. and –12° C., with 30 minute holds at the extreme temperatures) ice cream formulation 1 was rated 4.4 for texture, while ice cream formulations 2 and 3 both rated 5.2 on a 7-point hedonic scale. The advantage of the microcrystalline starch-based product, like the microcrystalline cellulose counterpart, is the improved smoothness and consistency of melt after prolonged storage. The microcrystalline starch-based product also modifies texture by increasing the sense of creaminess over the negative control (ice cream formulation 1).

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A microcrystalline starch-based product produced from retrograded and hydrolyzed starch and comprising microcrystalline starch, glucose and short chain glucooligosaccharides and having an average particle size of less than about 10 $\mu$.

2. A microcrystalline starch-based product according to claim 1, wherein the particle size is less than about 6 $\mu$.

3. A microcrystalline starch-based product comprising microcrystalline starch, glucose and short chain glucooligosaccharides and having an average particle size of less than about 10 $\mu$, produced by a process consisting of the steps of:
   a) incubating a hydrated starch dispersion under conditions sufficient for retrogradation of at least a portion of the starch to occur; and
   b) incubating a suspension of the product of step (a) with a catalyst under conditions sufficient for hydrolysis of amorphous starch regions to occur.

4. A microcrystalline starch-based product according to claim 3, wherein the process further consists of debranching the starch prior to or concurrent with step (a).

5. A microcrystalline starch-based product according to claim 3, wherein the process further consists of drying the product of step (b).

6. A method of preparing a microcrystalline starch-based product comprising microcrystalline starch, glucose and short chain glucooligosaccharides and having an average particle size of less than about 10 $\mu$, consisting of the steps of:
   a) incubating a hydrated starch dispersion under conditions sufficient for retrogradation of at least a portion of the starch to occur; and
   b) incubating a suspension of the product of step (a) with a catalyst under conditions sufficient for hydrolysis of amorphous starch regions to occur.

7. A method according to claim 6, further consisting of debranching the starch prior to or concurrent with step (a).

8. A method according to claim 6, further consisting of drying the product of step (b).

9. A method according to claim 6, wherein the catalyst of step (b) is glucoamylase or $\alpha$-amylase or a mixture thereof.

10. A method according to claim 6, wherein the starch has an amylose content of greater than about 30%.

11. A method according to claim 6, wherein the starch is selected from the group consisting of corn, wheat, rice, potatoes, tapioca, cassava or arrowroot, alant, amioca and sago.

12. A food or beverage containing a microcrystalline starch-based product comprising water-insoluble microcrystalline starch, glucose and short chain glucooligosaccharides and having an average particle size of less than about 10 $\mu$.

13. The food or beverage of claim 12 which is selected from the group consisting of cookies, breads, cakes, pies, noodles, fudge, brownies, low-fat margarine, snack dips, sour cream, mayonnaise, cream cheese, spreads, yogurt, milkshakes, ice cream, frozen desserts, crackers, graham crackers, pretzels, extruded cereals and extruded snacks.

14. A food or beverage wherein at least a portion of the sugar, fat or flour has been replaced by a microcrystalline starch-based product comprising water-insoluble microcrystalline starch, glucose and short chain glucooligosaccharides and having an average particle size of less than about 10 $\mu$.

15. A reduced-fat food or beverage wherein at least a portion of the fat has been replaced by a microcrystalline starch-based product comprising water-insoluble microcrystalline starch, glucose and short chain glucooligosaccharides and having an average particle size of less than about 10 $\mu$.

16. A frozen food or beverage containing a microcrystalline starch-based product comprising water-insoluble microcrystalline starch, glucose and short chain glucooligosaccharides and having an average particle size of less than about 10 $\mu$, which microcrystalline starch-based product inhibits ice crystal formation in the frozen food product.

17. The frozen food or beverage of claim 16, which is selected from the group consisting of ice cream, frozen yogurt, sherbet, ice milk and frozen desserts.

* * * * *